US010624597B2

(12) United States Patent
Nam et al.

(10) Patent No.: US 10,624,597 B2
(45) Date of Patent: Apr. 21, 2020

(54) MEDICAL IMAGING DEVICE AND MEDICAL IMAGE PROCESSING METHOD

(71) Applicants: SAMSUNG ELECTRONICS CO., LTD., Gyeonggi-do (KR); SEOUL NATIONAL UNIVERSITY R&DB FOUNDATION, Seoul (KR)

(72) Inventors: Woo-hyun Nam, Seoul (KR); Yong-sup Park, Seoul (KR); Yeong-gil Shin, Seoul (KR); Jae-sung Lee, Seoul (KR); Jin-wook Chung, Seoul (KR); Ji-hye Kim, Goyang-si (KR); Yong-geun Lee, Seoul (KR)

(73) Assignees: Samsung Electronics Co., Ltd., Suwon-si (KR); Seoul National University R&DB Foundation, Seoul (KR)

( * ) Notice: Subject to any disclaimer, the term of this patent is extended or adjusted under 35 U.S.C. 154(b) by 217 days.

(21) Appl. No.: 15/553,052

(22) PCT Filed: Feb. 17, 2016

(86) PCT No.: PCT/KR2016/001615
§ 371 (c)(1),
(2) Date: Aug. 23, 2017

(87) PCT Pub. No.: WO2016/137157
PCT Pub. Date: Sep. 1, 2016

(65) Prior Publication Data
US 2018/0055469 A1    Mar. 1, 2018

Related U.S. Application Data

(60) Provisional application No. 62/120,092, filed on Feb. 24, 2015.

(30) Foreign Application Priority Data

Feb. 26, 2015    (KR) .................. 10-2015-0027488

(51) Int. Cl.
*A61B 6/00*    (2006.01)
*G06T 7/30*    (2017.01)
(Continued)

(52) U.S. Cl.
CPC .............. *A61B 6/485* (2013.01); *A61B 6/466* (2013.01); *A61B 6/481* (2013.01); *A61B 6/504* (2013.01);
(Continued)

(58) Field of Classification Search
CPC ....... A61B 6/032; A61B 6/4441; A61B 6/463; A61B 6/466; A61B 6/481; A61B 6/485;
(Continued)

(56) References Cited

U.S. PATENT DOCUMENTS 7,787,683 B2    8/2010    Khamene et al.
9,563,949 B2    2/2017    Hwang et al.
(Continued)

FOREIGN PATENT DOCUMENTS

KR    10-2014-0032810 A    3/2014

OTHER PUBLICATIONS

Alejandro F. Franfi et al.; "Multiscale vessel enhancement filtering"; In Medical Image Computing and Computer-Assisted Intervention; pp. 130-137; Lecture Notes in Computer Science, vol. 1496; Image Sciences Institute, University Hospital Utrecht Room E.01.334, Heidelberglaan 100, 3584 CX Utrecht, the Netherlands.
(Continued)

*Primary Examiner* — Marcus H Taningco
(74) *Attorney, Agent, or Firm* — Jefferson IP Law, LLP

(57) ABSTRACT

A method of processing a medical image includes acquiring a three-dimensional (3D) medical image indicating a blood
(Continued)

vessel and a two-dimensional (2D) medical image indicating the blood vessel, determining a blood vessel area in the 3D medical image corresponding to a partial area of the blood vessel in the 2D medical image, and matching the blood vessel area with the partial area in the 2D medical image.

14 Claims, 12 Drawing Sheets

(51) Int. Cl.

| | | |
|---|---|---|
| *G06T 7/33* | (2017.01) | |
| *G16H 30/40* | (2018.01) | |
| *A61B 6/03* | (2006.01) | |
| *G06F 19/00* | (2018.01) | |
| *G06T 7/00* | (2017.01) | |

(52) U.S. Cl.
CPC .................. *G06T 7/30* (2017.01); *G06T 7/33* (2017.01); *G16H 30/40* (2018.01); *A61B 6/032* (2013.01); *A61B 6/4441* (2013.01); *A61B 6/463* (2013.01); *A61B 6/487* (2013.01); *G06F 19/321* (2013.01); *G06T 7/0012* (2013.01); *G06T 2200/04* (2013.01); *G06T 2207/10081* (2013.01); *G06T 2207/10116* (2013.01); *G06T 2207/30101* (2013.01); *G06T 2207/30172* (2013.01)

(58) Field of Classification Search
CPC ....... A61B 6/487; A61B 6/504; G06F 19/321; G06T 2200/04; G06T 2207/10081; G06T 2207/10116; G06T 2207/30101; G06T 2207/30172; G06T 7/0012; G06T 7/30; G06T 7/33; G16H 30/40
See application file for complete search history.

(56) References Cited

U.S. PATENT DOCUMENTS

| | | |
|---|---|---|
| 2005/0272992 A1 | 12/2005 | Odonnell et al. |
| 2010/0061603 A1* | 3/2010 | Mielekamp ............ A61B 6/466 382/128 |
| 2010/0246916 A1* | 9/2010 | Deuerling-Zheng ........................ A61B 6/481 382/131 |
| 2012/0177277 A1 | 7/2012 | Florent et al. |
| 2013/0094745 A1 | 4/2013 | Sundar |
| 2013/0116551 A1 | 5/2013 | Florent et al. |

OTHER PUBLICATIONS

Robert Van Uitert et al.; "Subvoxel precise skeletons of volumetric data based on fast marching methods"; pp. 627-638; vol. 34, No. 2; Feb. 2007; American Association of Physicists in Medicine.

\* cited by examiner

FIG. 3
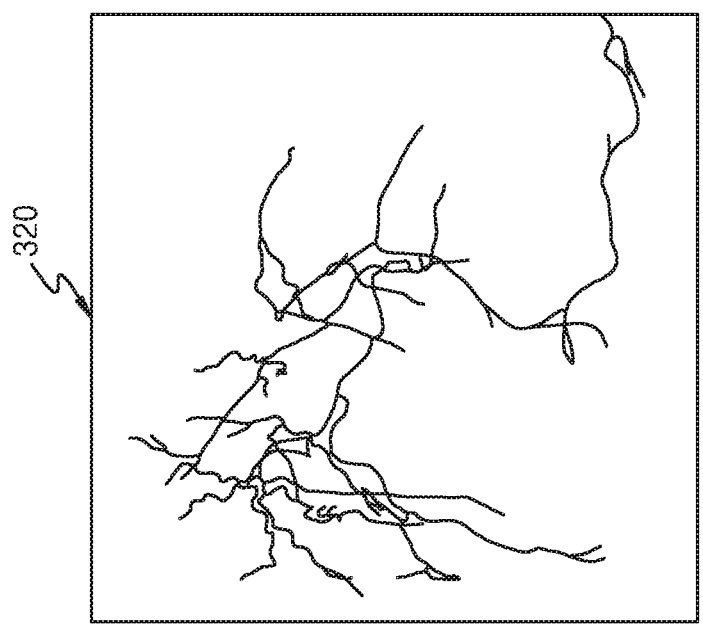
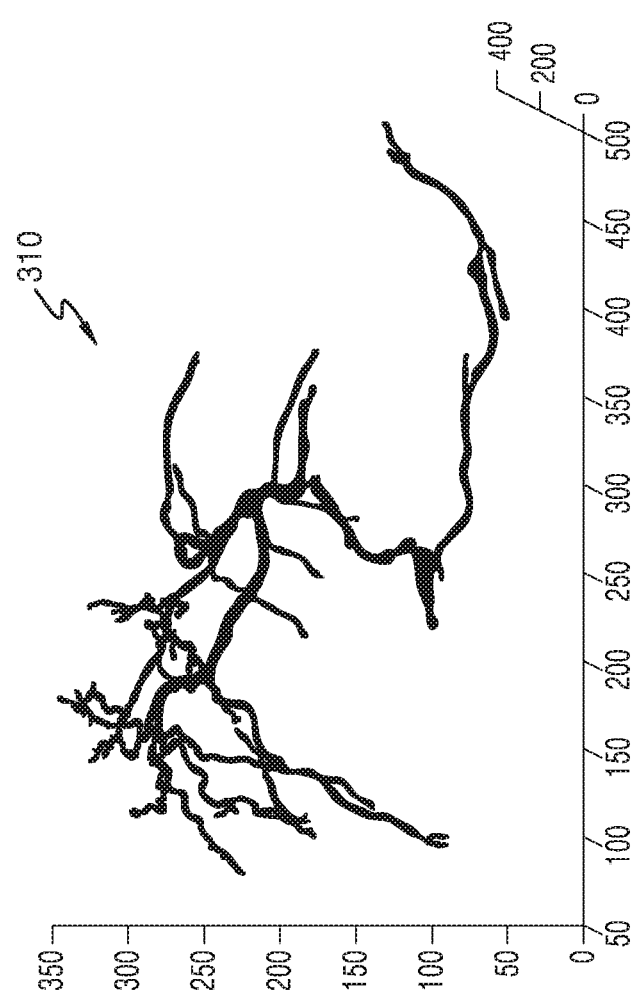

FIG. 4
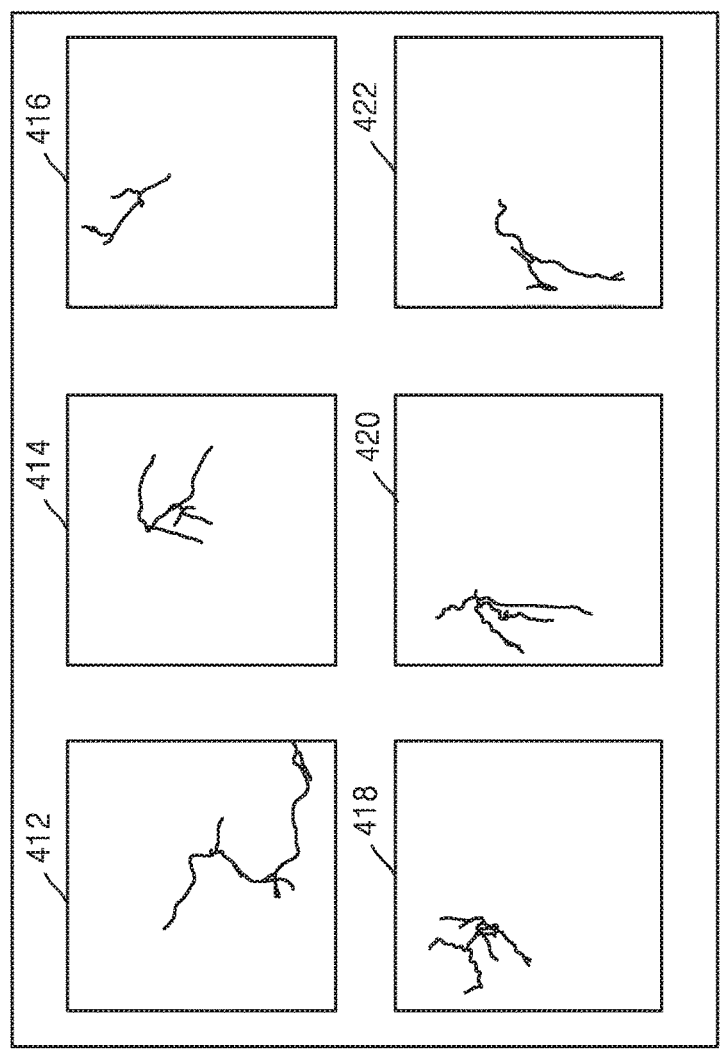
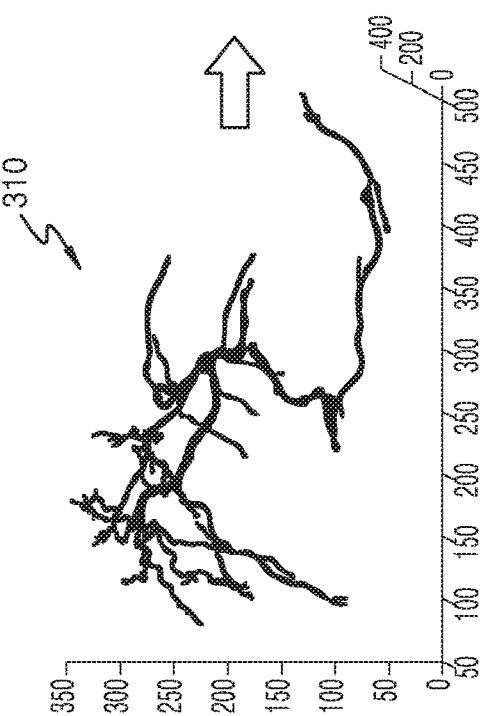

MEDICAL IMAGING DEVICE AND MEDICAL IMAGE PROCESSING METHOD

TECHNICAL FIELD

One or more exemplary embodiments relate to a medical imaging apparatus which matches a two-dimensional (2D) medical image and a three-dimensional (3D) medical image, and a method of processing a medical image.

BACKGROUND ART

A medical imaging apparatus is used to acquire an image of an internal structure of an object. The medical apparatus provides a user with medical information by imaging and processing structural details, internal tissues, or a fluid flow in a human body. A user, such as a medical doctor, may check and diagnose the health and disease state of a patient based on a medical image output from a medical imaging apparatus.

An X-ray apparatus that is an example of the medical imaging apparatus is a medical imaging apparatus used to acquire an image of an internal structure of a human body by transmitting an X-ray through the human body. Compared to other medical apparatuses such as a magnetic resonance imaging (MRI) apparatus or a CT apparatus, the X-ray apparatus has merit in that a medical image of an object may be acquired conveniently within a short time. Accordingly, the X-ray apparatus has been widely used for chest imaging, abdomen imaging, skeleton imaging, sinus imaging, neck soft tissue imaging, and breast imaging.

Fluoroscopy is an image processing technology used to acquire an X-ray motion picture by capturing an image of an object in real time. A user may use fluoroscopy to monitor X-ray angiography or a surgical operation.

DISCLOSURE

Technical Problem

One or more exemplary embodiments include a medical imaging apparatus which matches a two-dimensional (2D) medical image and a three-dimensional (3D) medical image, and a method of processing a medical image.

Technical Solution

According to one or more exemplary embodiments, a method of processing a medical image includes acquiring a three-dimensional (3D) medical image indicating a blood vessel and a two-dimensional (2D) medical image indicating the blood vessel, determining a blood vessel area in the 3D medical image corresponding to a partial area of the blood vessel in the 2D medical image, and matching the blood vessel area with the partial area in the 2D medical image.

The partial area may be any one of an area, into which a contrast agent is injected, in a blood vessel of the 2D medical image, a region of interest (ROI) in a blood vessel of the 2D medical image, and an area where a target object is located in a blood vessel of the 2D medical image.

The determining of the blood vessel area may include separating a 3D blood vessel area from the 3D medical image, separating the partial area from the 2D medical image, and determining a sub-blood vessel area having a highest similarity with the partial area as the blood vessel area, from among a plurality of sub-blood vessel areas divided from the 3D blood vessel area.

The determining of the blood vessel area may further include performing a translational or rotational movement on centerlines of each of the plurality of sub-blood vessel areas, calculating a distance between the translationally or rotationally moved centerlines of each of the plurality of sub-blood vessel areas and a centerline of the partial area, and determining a sub-blood vessel area having a distance of a minimum value from the partial area to be the blood vessel area.

The determining of the blood vessel area may further include projecting centerlines of each of the plurality of sub-blood vessel areas onto a 2D plane, calculating a distance between the projected centerline of each of the sub-blood vessel areas and a centerline of the partial area, and determining a sub-blood vessel area having a distance of a minimum value from the partial area to be the blood vessel area.

The calculating of the distance may includes generating a distance transform with respect to the centerline of the partial area, and calculating a distance between the projected centerline of each of the sub-blood vessel areas and the centerline of the partial area, by using the distance transform.

The matching of the blood vessel area with the partial area in the 2D medical image may include determining 3D transform information to match the blood vessel area with the partial area, and matching the blood vessel area with the partial area of the 2D medical image, based on the 3D transform information.

The method may further include storing a match image in which the blood vessel area is matched with the partial area of the 2D medical image, and displaying the match image.

The 3D medical image may be an image acquired through computed tomography (CT) angiography before performing a certain operation on an object, and the 2D medical image may be an image acquired through X-ray angiography during the operation performed on the object.

According to one or more exemplary embodiments, a medical imaging apparatus includes an image acquirer acquiring a three-dimensional (3D) medical image indicating a blood vessel and a two-dimensional (2D) medical image indicating the blood vessel, and a matching unit determining a blood vessel area in the 3D medical image corresponding to a partial area of the blood vessel in the 2D medical image, and matching the blood vessel area with the partial area of the 2D medical image.

According to one or more exemplary embodiments, computer readable recording medium having recorded thereon a program, which when executed by a computer, performs the method is provided.

Advantageous Effects

According to one or more exemplary embodiments, the medical imaging apparatus may determine a blood vessel area in the 3D medical image corresponding to the partial area of the blood vessel, into which a contrast agent is selectively injected, and generate a match image, and thus, may provide a 3D roadmap in which correction to various motions of an object is available. In addition, since the medical imaging apparatus may express the partial area of the blood vessel, into which a contrast agent is selectively injected, in a 3D blood vessel structure through a match image, convenience in convenience in performing an operation on an object may be improved.

DESCRIPTION OF DRAWINGS

FIG. 3 illustrates an example in which a medical imaging apparatus extracts a three dimensional (3D) blood vessel area or a centerline of the 3D blood vessel area from a 3D medical image;

FIGS. 4 and 5 illustrate an example in which a medical imaging apparatus divides a 3D blood vessel area into a plurality of sub-blood vessel areas;

BEST MODE

Figure 1:
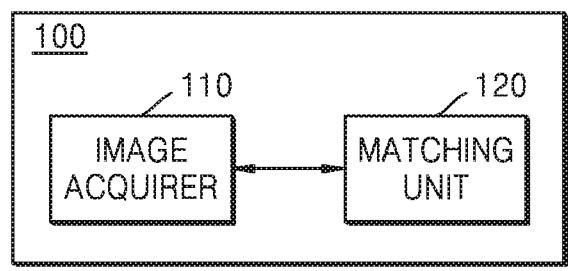
FIG. 1 is a block diagram of a medical imaging apparatus according to an exemplary embodiment.

According to one or more exemplary embodiments, a method of processing a medical image includes acquiring a three-dimensional (3D) medical image indicating a blood vessel and a two-dimensional (2D) medical image indicating the blood vessel, determining a blood vessel area in the 3D medical image corresponding to a partial area of the blood vessel in the 2D medical image, and matching the blood vessel area with the partial area in the 2D medical image.

According to one or more exemplary embodiments, a medical imaging apparatus includes an image acquirer acquiring a three-dimensional (3D) medical image indicating a blood vessel and a two-dimensional (2D) medical image indicating the blood vessel, and a matching unit determining a blood vessel area in the 3D medical image corresponding to a partial area of the blood vessel in the 2D medical image, and matching the blood vessel area with the partial area of the 2D medical image.

According to one or more exemplary embodiments, computer readable recording medium having recorded thereon a program, which when executed by a computer, performs the method is provided.

MODE FOR INVENTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present inventive concept will be described more fully with reference to the accompanying drawings, in which exemplary embodiments of the inventive concept are shown. This inventive concept may, however, be embodied in many different forms and should not be construed as limited to the exemplary embodiments set forth herein. Rather, these embodiments are provided so that this disclosure will be thorough and complete, and will fully convey the scope of the inventive concept to one of ordinary skill in the art. Sizes of components in the drawings may be exaggerated for convenience of explanation. In other words, since sizes and thicknesses of components in the drawings are arbitrarily illustrated for convenience of explanation, the following embodiments are not limited thereto.

The terms used in the present specification are briefly described and the present inventive concept is described in detail.

The terms used with respect to the present inventive concept have been selected from currently widely used general terms in consideration of the functions in the present inventive concept. However, the terms may vary according to the intention of one of ordinary skill in the art, case precedents, and the advent of new technologies. Also, for special cases, meanings of the terms selected by the applicant are described in detail in the description section. Accordingly, the terms used with respect to the present inventive concept are defined based on their meanings in relation to the contents discussed throughout the specification, not by their simple meanings.

When a part may "include" a certain constituent element, unless specified otherwise, it may not be construed to exclude another constituent element but may be construed to further include other constituent elements. Terms such as "~ portion", "~unit", "~ module", and "~ block" stated in the specification may signify a unit to process at least one function or operation and the unit may be embodied by hardware such as a field-programmable gate array (FPGA) or an application-specific integrated circuit (ASIC), software, or a combination of hardware and software. However, the unit may be configured to be located in a storage unit medium to be addressed or configured to be able to operate one or more processors. Accordingly, the unit as an example includes constituent elements such as software constituent elements, object-oriented software constituent elements, class constituent elements, and task constituent elements, processes, functions, attributes, procedures, sub-routines, segments of program codes, drivers, firmware, microcodes, circuits, data, databases, data structures, tables, arrays, and variables. The constituent elements and functions provided by the "units" may be combined into a smaller number of constituent elements and units or may be further divided into additional constituent elements and units. Accordingly, the present inventive concept is not limited by a specific combination of hardware and software.

In the present specification, an "image" may signify multi-dimensional data formed of discrete image elements, for example, pixels in a two-dimensional (2D) image and voxels in a three-dimensional (3D) image. For example, an image may include an X-ray, a computed tomography (CT) image, a magnetic resonance imaging (MRI) image, an ultrasound image, and a medical image of an object acquired by other medical imaging apparatuses.

Also, in the present specification, an "object" may include a human, an animal, or a part of a human or an animal. For example, an object may include organs such as the liver, the heart, the womb, the brain, a breast, the abdomen, etc., or blood vessels. Also, an object may include a phantom that signifies matter having a volume that is approximately the intensity and effective atomic number of a living thing, and may include a sphere phantom having a property similar to a human body.

Also, in the present specification, a "user" may be a doctor, a nurse, a clinical pathologist, a medical imaging expert, a technician who fixes a medical apparatus, etc, but the present inventive concept is not limited thereto.

FIG. 1 is a block diagram of a medical imaging apparatus 100 according to an exemplary embodiment.

Referring to FIG. 1, the medical imaging apparatus 100 according to the present exemplary embodiment may include an image acquirer 110 and a matching unit 120. In FIG. 1, only constituent elements of the medical imaging apparatus 100 related to the present exemplary embodiment are illustrated. Accordingly, one of ordinary skill in the art to which the present inventive concept pertains may understand that other general constituent elements may be further included in addition to the constituent elements illustrated in FIG. 1.

The image acquirer 110 acquires a 3D medical image and a 2D medical image indicating a blood vessel, according to an exemplary embodiment. According to the present exemplary embodiment, the image acquirer 110 may perform CT angiography or MRI angiography on an object and acquire a 3D medical image indicating a blood vessel in the object in 3D. Furthermore, according to the present exemplary embodiment, the image acquirer 110 may perform X-ray angiography on a blood vessel in the object and acquire a 2D medical image indicating the blood vessel in the object in 2D. Furthermore, according to the present exemplary embodiment, a 2D medical image may be an X-ray motion picture acquired through fluoroscopy. According to the present exemplary embodiment, the 3D medical image may be acquired by the image acquirer 110 in advance before a user performs a certain operation on an object, and the 2D medical image may be acquired by the image acquirer 110 in real time while the user performs the operation on the object. Furthermore, according to the present exemplary embodiment, the image acquirer 110 may acquire the 3D medical image and the 2D medical image indicating a blood vessel from the outside through a communication unit (not shown). Furthermore, according to the present exemplary embodiment, the image acquirer 110 may acquire from a memory (not shown) the 3D medical image and the 2D medical image that are previously stored.

The matching unit 120 according to the present exemplary embodiment determines a blood vessel area in the 3D medical image corresponding to a partial area of a blood vessel in the 2D medical image.

According to the present exemplary embodiment, the partial area of the blood vessel in the 2D medical image may be an area of a blood vessel, into which a contrast agent is injected. For example, the user may inject a contrast agent into a blood vessel of an object and then the image acquirer 110 performs X-ray angiography. As a result, the 2D medical image may indicate a portion into which the contrast agent is injected, as the partial area of a blood vessel. Furthermore, according to the present exemplary embodiment, the partial area of the blood vessel in the 2D medical image may be a region of interest (ROI) set by the user. Furthermore, according to the present exemplary embodiment, the partial area of the blood vessel in the 2D medical image may be an area of the blood vessel where a target object is located. For example, when the user inserts a catheter into the blood vessel of the object, the partial area of the blood vessel may be an area where the catheter is located.

The matching unit 120 may separate or extract a 3D blood vessel area from the 3D medical image, according to the present exemplary embodiment. In other words, the matching unit 120 may separate or extract only a blood vessel area displayed in 3D in the 3D medical image. Next, the matching unit 120 may divide the separated 3D blood vessel area into a plurality of sub-blood vessel areas.

The matching unit 120 may generate a graph corresponding to the 3D blood vessel area, based on a branch point of the blood vessel, according to the present exemplary embodiment. In other words, the matching unit 120 may generate a graph showing a connection relation between the branch points of each blood vessel in the 3D blood vessel area. Next, the matching unit 120 may divide the graph corresponding to the 3D blood vessel area into a plurality of areas according to a certain condition. An example of the condition may be that a sum of the distances between the branch points included in the respective areas is greater than a certain critical value. Accordingly, the matching unit 120 may divide the graph into a plurality of areas, in particular, the 3D blood vessel area corresponding to the graph into a plurality of sub-blood vessel areas corresponding to the areas. A detailed exemplary embodiment is described below with reference to FIGS. 4 and 5.

The matching unit 120 according to the present exemplary embodiment may separate the partial area of the blood vessel from the 2D medical image. In other words, the matching unit 120 may separate only the partial area of the blood vessel displayed in 2D from the 2D medical image. Furthermore, according to the present exemplary embodiment, when the 2D medical image is a motion picture formed of a plurality of frames, the matching unit 120 may separate the partial area of the blood vessel based on the 2D medical images corresponding to the frames. For example, the matching unit 120 may separate the partial area of the blood vessel from the 2D medical image corresponding to a current frame, referring to a partial area of a blood vessel displayed in a 2D medical image corresponding to a next frame.

The matching unit 120 according to the present exemplary embodiment may determine a sub-blood vessel area corresponding to the partial area of the blood vessel in the 2D medical image, from among the sub-blood vessel areas divided from the 3D blood vessel area. In other words, the matching unit 120 may determine a sub-blood vessel area having a highest similarity with the partial area of the blood vessel, from among the sub-blood vessel areas.

According to the present exemplary embodiment, the matching unit 120 may project centerlines of each of the sub-blood vessels on a 2D plane. The matching unit 120 according to the present exemplary embodiment may calculate a distance between a centerline of each of the sub-blood vessel areas projected on the 2D plane and a centerline of the partial area of the blood vessel in the 2D medical image. According to the present exemplary embodiment, the matching unit 120 may calculate the closest distance from the centerline of the partial area of the blood vessel for each point forming a centerline of a certain sub-blood vessel area. The matching unit 120 may determine an average of the closest distances calculated for each point to be a distance between the centerline of a certain sub-blood vessel area and the centerline of the partial area of the blood vessel.

According to the present exemplary embodiment, since the distance between the centerline of a certain sub-blood vessel area of the sub-blood vessel areas and the centerline of the partial area of the blood vessel in the 2D medical image may vary according to how a centerline of a certain sub-blood vessel area is moved or rotated in a 3D space, the matching unit 120 may perform a translational or rotational movement with respect to the centerline of the sub-blood vessel area a preset number of times by varying a value, which represents a degree of the translational or rotational movement, within a preset range. Next, the matching unit 120 may calculate the distance between the translationally or rotationally moved centerline of a certain sub-blood vessel area and the centerline of the partial area of the blood vessel by the preset number of times. As a result, the matching unit 120 may determine the distance having a minimum value from among the distances calculated the preset number of times, to be the distance between the centerline of a certain sub-blood vessel area and the centerline of the partial area of the blood vessel. Furthermore, according to the present exemplary embodiment, the matching unit 120 may store information about the translational or rotational movement with respect to the sub-blood vessel area corresponding to the distance having the minimum value, in the form of a matrix.

According to the present exemplary embodiment, in order to facilitate the calculation of the distance between the centerline of each of the sub-blood vessel areas and the centerline of the partial area of the blood vessel, the matching unit 120 may generate a distance transform such as a distance map or a distance field with respect to the centerline of the partial area of the blood vessel. According to the present exemplary embodiment, the distance transform may be presented as an image and may include information about the position of the centerline of the centerline of the partial area of the blood vessel for each pixel in the image. Accordingly, the matching unit 120 may increase a speed of calculation of the distance between the centerline of each of the sub-blood vessel areas and the centerline of the partial area of the blood vessel, by using the distance transform with respect to the centerline of the partial area of the blood vessel, and the centerlines of each of the sub-blood vessel areas.

The matching unit 120 according to the present exemplary embodiment may calculate the distance between the centerline of each of the sub-blood vessel areas and the centerline of the partial area of the blood vessel in the 2D medical image, and may determine a sub-blood vessel area having the minimum distance from the partial area of the blood vessel, from among the sub-blood vessel areas. Accordingly, the matching unit 120 may determine the sub-blood vessel area having the minimum distance from the partial area of the blood vessel, to be the blood vessel area in the 3D medical image having the highest similarity with the partial area of the blood vessel. A detailed exemplary embodiment is described below with reference to FIG. 7.

The matching unit 120 according to the present exemplary embodiment may match the blood vessel area in the 3D medical image having the highest similarity with the partial area of the blood vessel in the 2D medical image, with the 2D medical image. According to the present exemplary embodiment, the matching unit 120 may determine transform information to match the blood vessel area in the 3D medical image with the partial area of the blood vessel in the 2D medical image. A transformation matrix may be an example of the transform information. According to the present exemplary embodiment, the matching unit 120 may determine a transformation matrix to match the sub-blood vessel area in the 3D medical image with the partial area of the blood vessel in the 2D medical image, based on the information about translational or rotational movement performed on the sub-blood vessel area having the minimum distance from the partial area of the blood vessel in the sub-blood vessel areas. In other words, the matching unit 120 may determine the transformation matrix to more precisely match the blood vessel area in the 3D medical image with the partial area of the blood vessel in the 2D medical image, by adding or subtracting a change amount within a preset range with respect to each figure of the matrix indicating the translational or rotational movement performed on the sub-blood vessel area. Accordingly, the matching unit 120 may match the blood vessel area in the 3D medical image having the highest similarity with the partial area of the blood vessel with the partial area of the blood vessel in the 2D medical image, by using the determined transformation matrix. In addition, the matching unit 120 may generate a match image in which the blood vessel area in the 3D medical image is matched with the 2D medical image.

Furthermore, according to the present exemplary embodiment, the matching unit 120 may match a blood vessel area larger than the blood vessel area in the 3D medical image having the highest similarity with the partial area of the blood vessel with the 2D medical image, according to a user's selection.

The medical imaging apparatus 100 or 200 may determine a blood vessel area in the 3D medical image corresponding to the partial area of the blood vessel, into which a contrast agent is selectively injected, and generate a match image, and thus, may provide a 3D roadmap in which correction to various motions of an object is available. In addition, since the medical imaging apparatus 100 or 200 may express the partial area of the blood vessel, into which a contrast agent is selectively injected, in a 3D blood vessel structure through a match image, convenience in performing an operation on an object may be improved.

Figure 2:
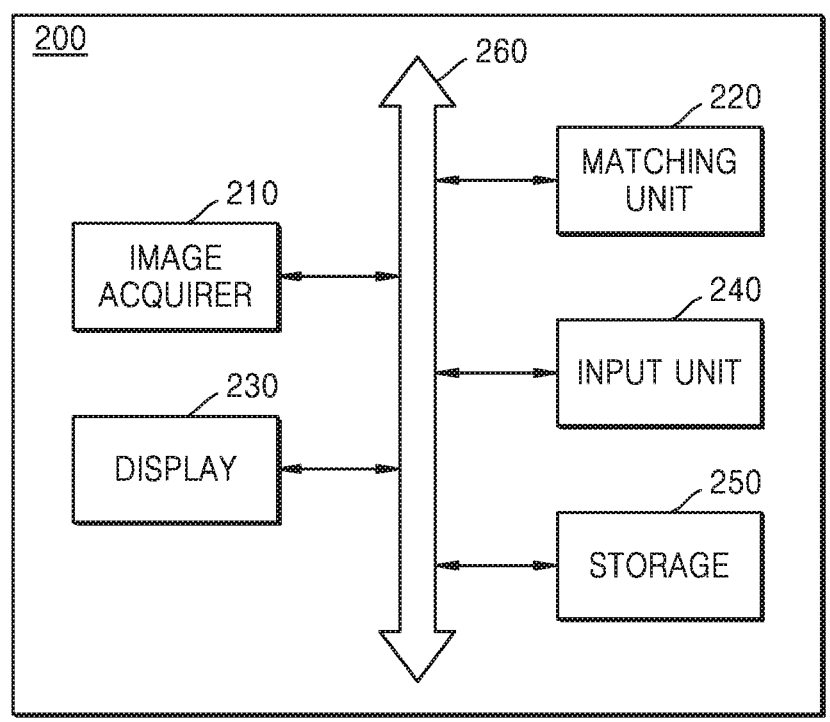
FIG. 2 is a block diagram of a medical imaging apparatus according to another exemplary embodiment.

FIG. 2 is a block diagram of a medical imaging apparatus 200 according to another exemplary embodiment.

Referring to FIG. 2, the medical imaging apparatus 200 according to the present exemplary embodiment may include an image acquirer 210, a matching unit 220, a display 230, an input unit 240, and a storage unit 250. Since the image acquirer 210 and the matching unit 220 may be applied to the exemplary embodiment described in FIG. 1, redundant descriptions thereof are omitted. In addition, the elements included in the medical imaging apparatus 200 may be connected to one another by using various types of connection technique 260 such as a wired method or wireless method.

The display 230 according to the present exemplary embodiment may display a match image generated by the matching unit 220. For example, the display 230 may display a match image or a user interface (UI) or a graphical user interface (GUI) related to function setting of the medical imaging apparatus 200.

The display 230 may include at least one of a liquid crystal display (LCD), a thin film transistor-liquid crystal display (TFT-LCD), an organic light-emitting diode (OLED), a flexible display, a 3D display, and an electrophoretic display. The medical imaging apparatus 200 may include two or more displays 230 according to an implementation form of the medical imaging apparatus 200.

The input unit 240 according to the present exemplary embodiment may receive a command to control the medical imaging apparatus 200 from a user. The input unit 240 according to the present exemplary embodiment may receive a command to match a blood vessel area in the 3D medical image with a 2D medical image from the user. Furthermore, according to the present exemplary embodiment, the display 230 and the input unit 240 may provide a UI for manipulating the medical imaging apparatus 200 to the user. The display 230 may display the UI.

The storage unit 250 according to the present exemplary embodiment may store the 2D medical image or the 3D medical image acquired by the image acquirer 210. In addition, the storage unit 250 may store the match image generated by the matching unit 220.

FIG. 3 illustrates an example in which the medical imaging apparatus 100 or 200 extracts a 3D blood vessel area or a centerline of the 3D blood vessel area from a 3D medical image.

The medical imaging apparatus 100 or 200 according to the exemplary embodiment may extract or separate a 3D blood vessel area 310 indicating only a blood vessel area from a 3D medical image of an object. Furthermore, according to the present exemplary embodiment, the medical imaging apparatus 100 or 200 may acquire the 3D blood vessel area 310 as a 3D medical image of the object.

In addition, the medical imaging apparatus 100 or 200 according to the present exemplary embodiment may extract a centerline 320 corresponding to the 3D blood vessel area 310 from the 3D blood vessel area 310 or the 3D medical image.

Figure 5:
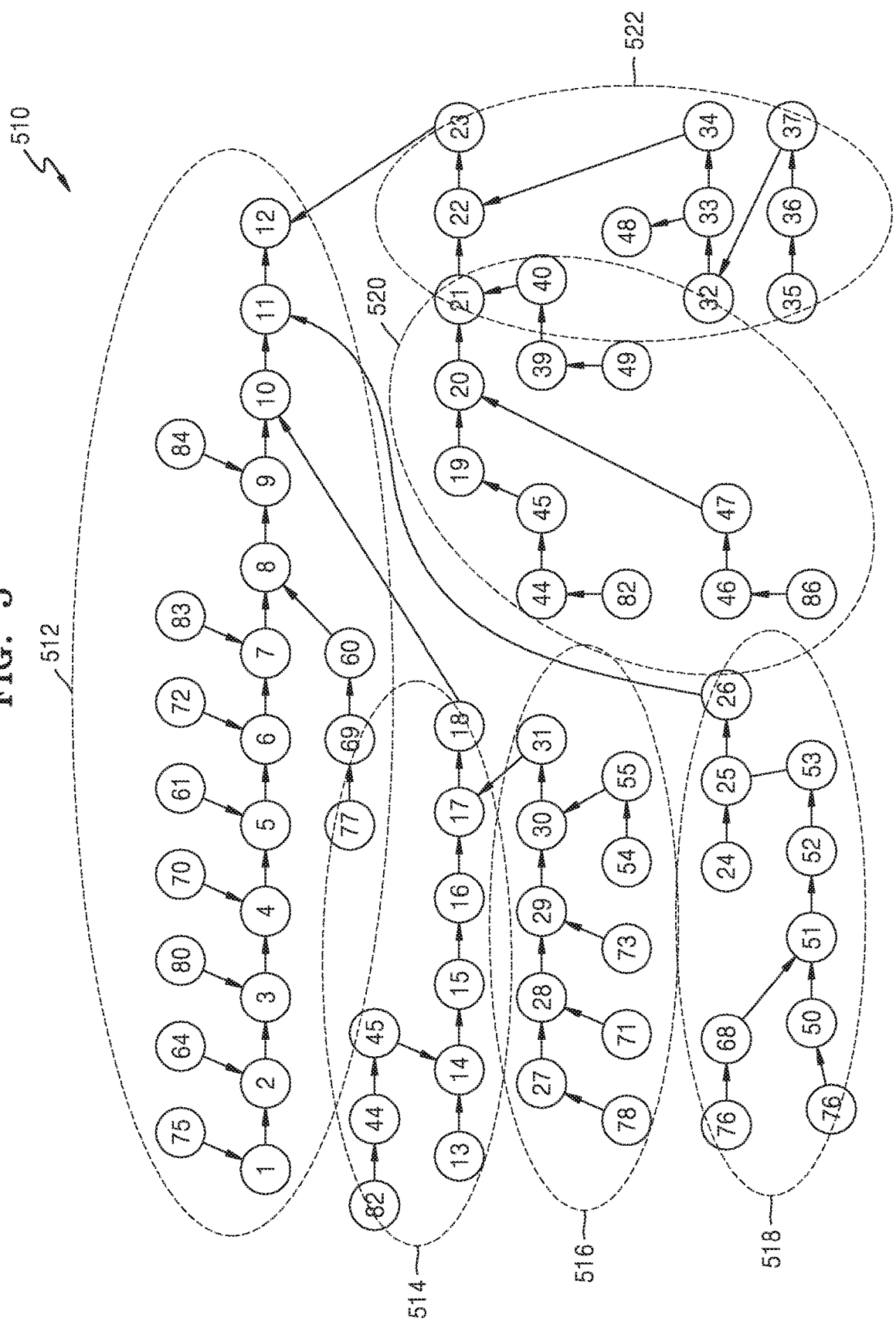

FIGS. 4 and 5 illustrate an example in which the medical imaging apparatus 100 or 200 divides a 3D blood vessel area into a plurality of sub-blood vessel areas.

The medical imaging apparatus 100 or 200 according to the present exemplary embodiment may divide the 3D blood vessel area 310 into a plurality of sub-blood vessel areas 412, 414, 416, 418, 420, and 422.

Referring to FIG. 5, the medical imaging apparatus 100 or 200 may generate a graph 510 showing a connection relation between branch points in each blood vessel in the 3D blood vessel area 310 of FIG. 3. In addition, the medical imaging apparatus 100 or 200 may generate the graph 510 showing a connection relation between branch points of each blood vessel in the centerline 320 corresponding to the 3D blood vessel area 310 of FIG. 3. In other words, as illustrated in FIG. 5, the medical imaging apparatus 100 or 200 may determine the number of the branch points of the respective blood vessels in the 3D blood vessel area 310 to be 86, and generate the graph 510 indicating the connection relation between the 86 branch points. Next, the medical imaging apparatus 100 or 200 may divide the graph 510 into a plurality of areas 512, 514, 516, 518, 520, and 522 according to a certain standard. According to the present exemplary embodiment, when the number of branch points in a certain area divided with respect to a certain branch point or a sum of a distance between branch points in a certain area is greater than a certain critical value, the medical imaging apparatus 100 or 200 may determine the certain area to be one area of the areas. Accordingly, the medical imaging apparatus 100 or 200 may divide the graph 510 into the areas 512, 514, 516, 518, 520, and 522. The medical imaging apparatus 100 or 200 may divide the 3D blood vessel area 310 corresponding to the graph 510 the sub-blood vessel areas 412, 414, 416, 418, 420, and 422 corresponding to the areas 512, 514, 516, 518, 520, and 522.

Figure 6:
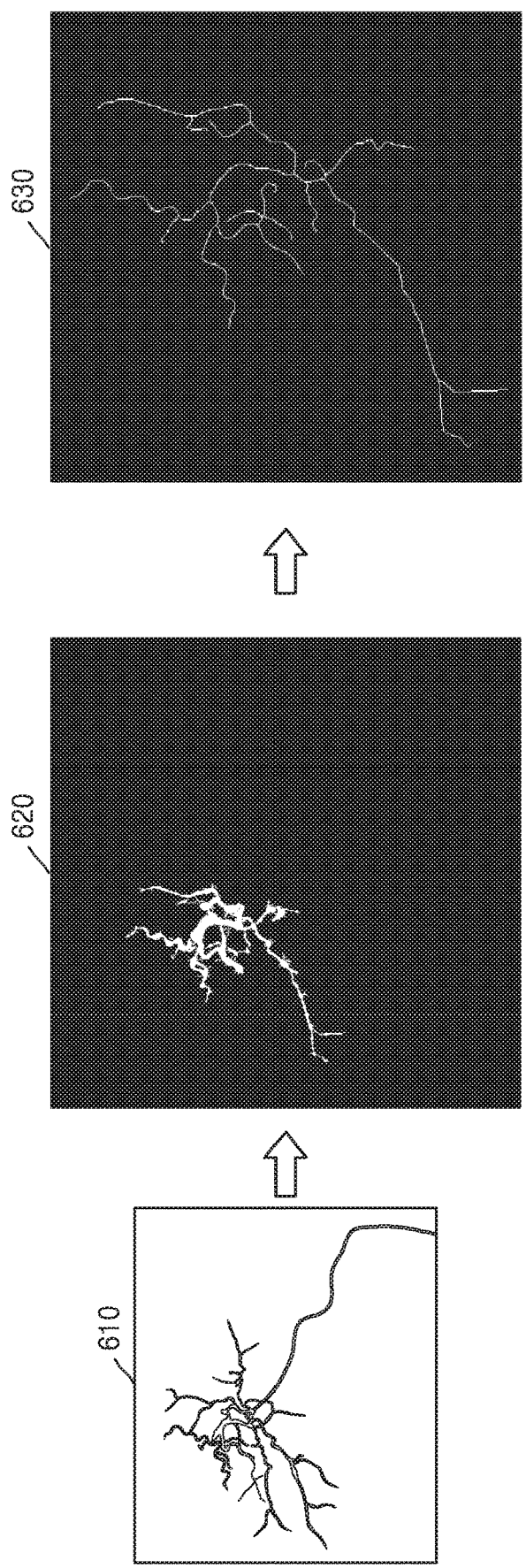
FIG. 6 illustrates an example in which a medical imaging apparatus separates a partial area of a blood vessel from a 2D medical image, according to an exemplary embodiment.

FIG. 6 illustrates an example in which the medical imaging apparatus 100 or 200 separates a partial area of a blood vessel from a 2D medical image, according to an exemplary embodiment.

The medical imaging apparatus 100 or 200 according to the present exemplary embodiment may extract or separate a partial area 620 of a blood vessel from a 2D medical image 610. In addition, the medical imaging apparatus 100 or 200 may extract a centerline 630 corresponding to the partial area 620 of the blood vessel, from the partial area 620 of the blood vessel.

Figure 7:
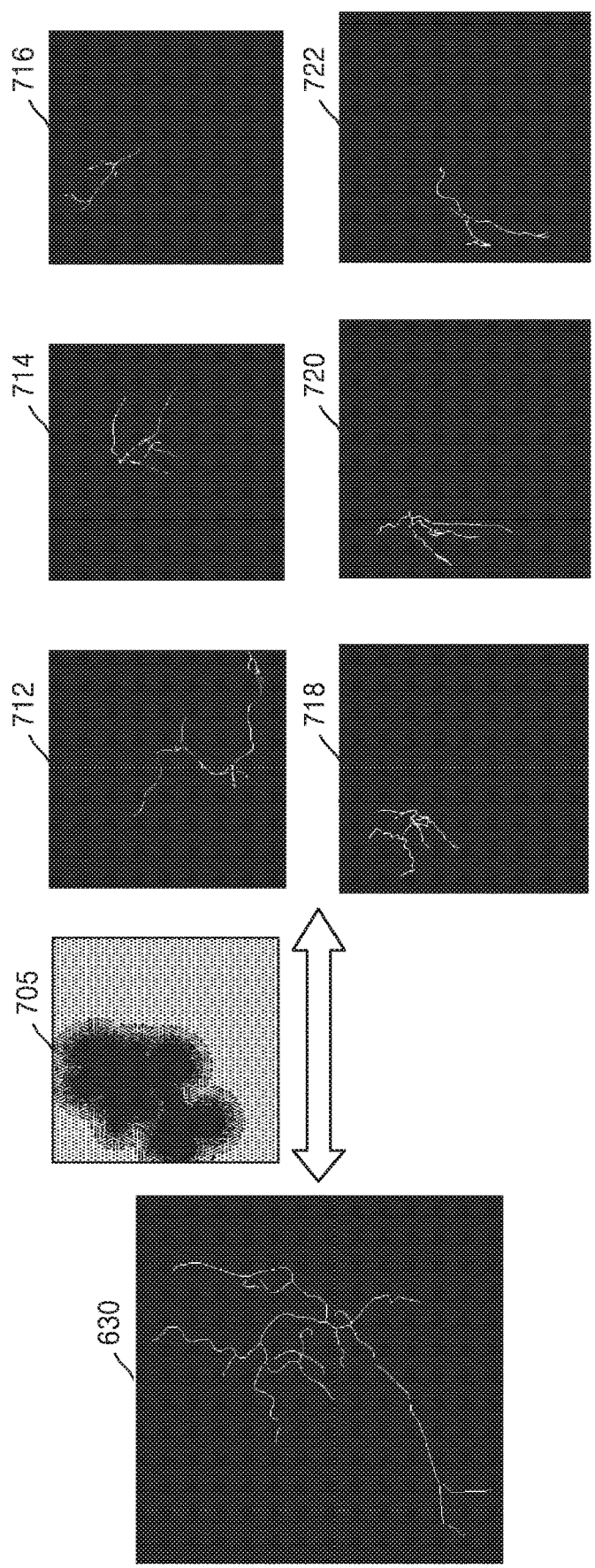
FIG. 7 illustrates an example in which a medical imaging apparatus determines a sub-blood vessel area having a highest similarity with the partial area of a blood vessel, from among the sub-blood vessel areas.

FIG. 7 illustrates an example in which the medical imaging apparatus 100 or 200 determines a sub-blood vessel area having the highest similarity with the partial area of a blood vessel, from among the sub-blood vessel areas.

The medical imaging apparatus 100 or 200 may extract the centerlines 712, 714, 716, 718, 720, and 722 respectively from the sub-blood vessel areas 412, 414, 416, 418, 420, and 422 of FIG. 4. In other words, the medical imaging apparatus 100 or 200 may extract the centerlines 712, 714, 716, 718, 720, and 722 respectively corresponding to the sub-blood vessel areas 412, 414, 416, 418, 420, and 422.

The medical imaging apparatus 100 or 200 according to the present exemplary embodiment may calculate distances between the centerline 630 corresponding to the partial area 620 of the blood vessel and each of the centerlines 712, 714, 716, 718, 720, and 722 respectively corresponding to the sub-blood vessel areas 412, 414, 416, 418, 420, and 422, to determine a sub-blood vessel area corresponding to the partial area 620 of the blood vessel. In addition, the medical imaging apparatus 100 or 200 may perform a translational or rotational movement with respect to each of the centerlines 712, 714, 716, 718, 720, and 722 by a preset number of times by varying a figure within a preset range. Next, the medical imaging apparatus 100 or 200 may project the translationally or rotationally moved centerlines 712, 714, 716, 718, 720, and 722 onto a 2D plane. Next, the medical imaging apparatus 100 or 200 may calculate, by a preset number of times, the distances between each of the centerlines 712, 714, 716, 718, 720, and 722 that have been projected onto a 2D plane and the centerline 630 corresponding to the partial area 620 of the blood vessel, and consequently, determine a centerline 718 having the minimum distance from the centerline 630 by comparing the distances calculated by the preset number of timed. Accordingly, the medical imaging apparatus 100 or 200 may determine the sub-blood vessel area 418 corresponding to the centerline 718 to be a sub-blood vessel area having the highest similarity with the partial area 620 of the blood vessel.

Furthermore, according to the present exemplary embodiment, the medical imaging apparatus 100 or 200 may generate a distance transform 705 with respect to the centerline 630 corresponding to the partial area 620 of the blood vessel, and facilitate calculation of the distances between each of the centerlines 712, 714, 716, 718, 720, and 722 and the centerline 630 by using the distance transform 705 and the centerlines 712, 714, 716, 718, 720, and 722.

Figure 8:
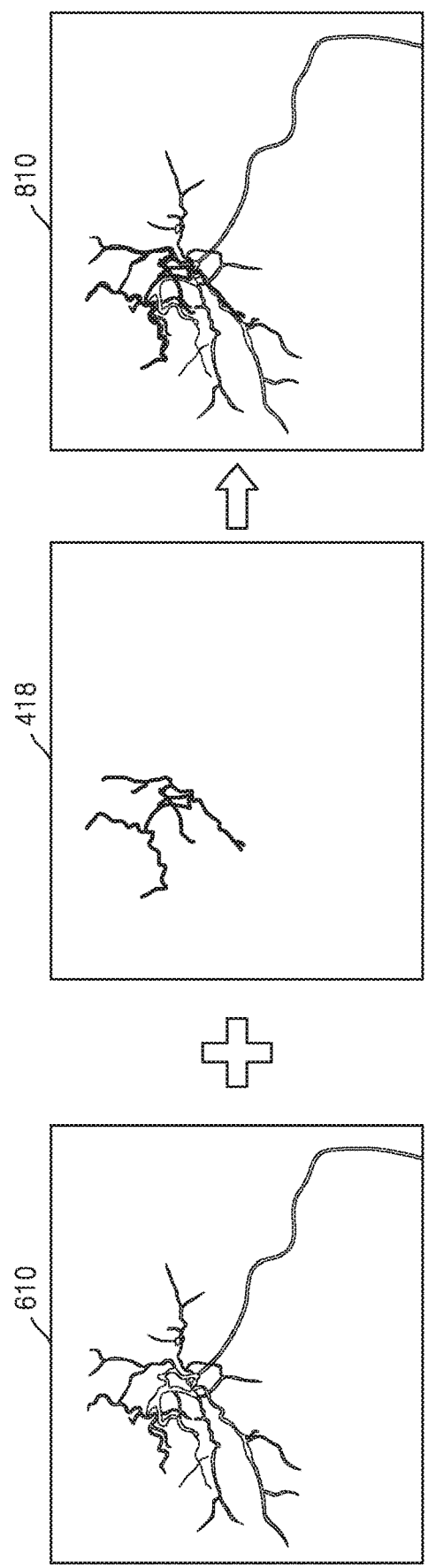
FIG. 8 illustrates an example of matching a blood vessel area in a 3D medical image with a 2D medical image, according to an exemplary embodiment.

FIG. 8 illustrates an example of matching a blood vessel area in a 3D medical image with a 2D medical image, according to an exemplary embodiment.

As described in FIG. 7, the medical imaging apparatus 100 or 200 according to the present exemplary embodiment may determine a sub-blood vessel area 418 to be a blood vessel area in the 3D medical image that is the most similar to the partial area 620 of the blood vessel extracted from the 2D medical image 610.

The medical imaging apparatus 100 or 200 according to the present exemplary embodiment may match the sub-blood vessel area 418 with the partial area 620 of the blood vessel in the 2D medical image 610. Accordingly, the medical imaging apparatus 100 or 200 may generate a match image 810 in which the sub-blood vessel area 418 is matched with the 2D medical image 610.

The medical imaging apparatus 100 or 200 according to the present exemplary embodiment may determine a transformation matrix to match the sub-blood vessel area 418 with the partial area 620 of the blood vessel in the 2D medical image 610. According to the present exemplary embodiment, the medical imaging apparatus 100 or 200 may determine the transformation matrix based on the information about the translational or rotational movement performed on the centerline 718. In other words, the medical imaging apparatus 100 or 200 may determine the transformation matrix to more precisely match the sub-blood vessel area 418 with the partial area 620 of the blood vessel in the 2D medical image 610 by adding or subtracting a change amount within a preset range with respect to each figure of a matrix indicating the translational or rotational movement performed on the centerline 718. Accordingly, the matching unit 120 may match the sub-blood vessel area 418 with the 2D medical image 610 by using the determined transformation matrix.

Figure 9:
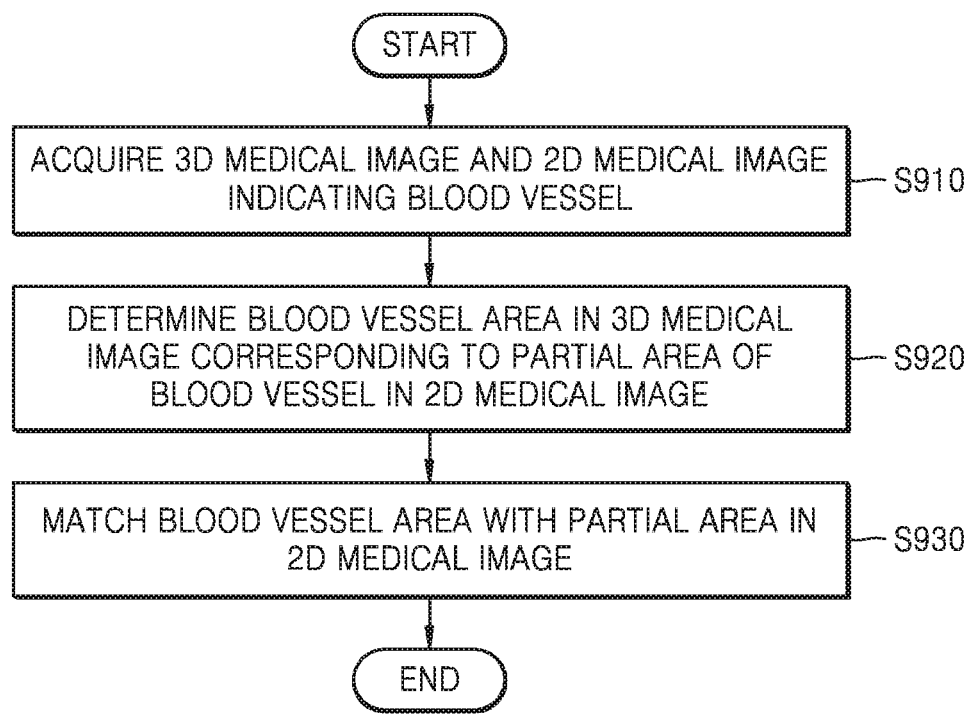
FIG. 9 is a flowchart for explaining a method, performed by a medical imaging apparatus, of processing a medical image, according to an exemplary embodiment.

FIG. 9 is a flowchart for explaining a method of processing a medical image performed by the medical imaging apparatus 100 or 200, according to an exemplary embodiment.

The method of FIG. 9 may be performed by the constituent elements of the medical imaging apparatus 100 or 200 of FIG. 1 or 2, and redundant descriptions thereof are omitted.

In S910, the medical imaging apparatus 100 or 200 acquires a 3D medical image and a 2D medical image indicating a blood vessel. According to the present exemplary embodiment, the medical imaging apparatus 100 or 200 may acquire a 3D medical image indicating a blood vessel in an object in 3D by performing CT angiography or MRI angiography on the object. Furthermore, according to the present exemplary embodiment, the medical imaging apparatus 100 or 200 may acquire a 2D medical image indicating the blood vessel in the object in 2D by performing X-ray angiography on the blood vessel in the object. Furthermore, according to the present exemplary embodiment, the medical imaging apparatus 100 or 200 may acquire a 3D medical image and a 2D medical image indicating a blood vessel from the outside. Furthermore, according to the present exemplary embodiment, the medical imaging apparatus 100 or 200 may acquire from an internal memory a 3D medical image and a 2D medical image that are previously stored.

In S920, the medical imaging apparatus 100 or 200 determines a blood vessel area in the 3D medical image corresponding to a partial area of the blood vessel in the 2D medical image.

According to the present exemplary embodiment, the partial area of the blood vessel in the 2D medical image may be an area of a blood vessel, into which a contrast agent is injected. For example, a user may inject a contrast agent into a blood vessel of an object, and the image acquirer 110 may perform X-ray angiography. As a result, a 2D medical image may indicate a portion into which the contrast agent is injected, as a partial area of the blood vessel. Furthermore, according to the present exemplary embodiment, the partial area of the blood vessel in the 2D medical image may be a ROI set by the user. Furthermore, according to the present exemplary embodiment, the partial area of the blood vessel in the 2D medical image may be an area of a blood vessel where a target object is located. For example, when the user inserts a catheter into the blood vessel, the partial area of the blood vessel may be an area where the catheter is located.

The medical imaging apparatus 100 or 200 according to the present exemplary embodiment may separate or extract a 3D blood vessel area from the 3D medical image. In other words, the medical imaging apparatus 100 or 200 may separate or extract only a blood vessel area that is displayed in 3D, from the 3D medical image. Next, the medical imaging apparatus 100 or 200 may divide the separated 3D blood vessel area into a plurality of sub-blood vessel areas.

The medical imaging apparatus 100 or 200 according to the present exemplary embodiment may generate a graph showing a connection relation between branch points of each blood vessel in the 3D blood vessel area. Next, the medical imaging apparatus 100 or 200 may divide the graph corresponding to the 3D blood vessel area into a plurality of areas according to a certain condition. An example of the condition may be that a sum of the distances between the branch points included in the respective areas is greater than a certain critical value. Accordingly, the medical imaging apparatus 100 or 200 may divide the graph into a plurality of areas, in particular, the 3D blood vessel area corresponding to the graph into a plurality of sub-blood vessel areas corresponding to the areas.

The medical imaging apparatus 100 or 200 according to the present exemplary embodiment may separate or extract the partial area of the blood vessel from the 2D medical image. In other words, the medical imaging apparatus 100 or 200 may separate or extract only the partial area of the blood vessel displayed in 2D from the 2D medical image.

The medical imaging apparatus 100 or 200 according to the present exemplary embodiment may determine a sub-blood vessel area corresponding to the partial area of the blood vessel in the 2D medical image, from among the sub-blood vessel areas divided from the 3D blood vessel area. In other words, the medical imaging apparatus 100 or 200 may determine a sub-blood vessel area having the highest similarity with the partial area of the blood vessel, from among the sub-blood vessel areas.

According to the present exemplary embodiment, the medical imaging apparatus 100 or 200 may project centerlines of each of the sub-blood vessels onto a 2D plane. The medical imaging apparatus 100 or 200 according to the present exemplary embodiment may calculate a distance between the centerline of each of the sub-blood vessel areas projected onto a 2D plane and the centerline of the partial area of the blood vessel. According to the present exemplary embodiment, the medical imaging apparatus 100 or 200 may calculate the shortest distance from the centerline of the partial area of the blood vessel, for each point forming the centerline of a certain sub-blood vessel area, and determine an average of the calculated shortest distances for each point, to be the distance between the centerline of a certain sub-blood vessel area and the centerline of the partial area of the blood vessel.

According to the present exemplary embodiment, the medical imaging apparatus 100 or 200 may perform a translational or rotational movement on the centerline of a certain sub-blood vessel area by a preset number of times by varying a figure within a preset range. Next, the medical imaging apparatus 100 or 200 may calculate the distance between the translationally or rotationally moved centerline of a certain sub-blood vessel area and the centerline of the partial area of the blood vessel by the preset number of times. As a result, the medical imaging apparatus 100 or 200 may determine the minimum distance from among the distances calculated by the preset number of times, to be the distance between the centerline of a certain sub-blood vessel area and the centerline of the partial area of the blood vessel.

According to the present exemplary embodiment, in order to facilitate the calculation of the distance between the centerline of each of the sub-blood vessel areas and the centerline of the partial area of the blood vessel in the 2D medical image, the medical imaging apparatus 100 or 200 may generate a distance transform such as a distance map or a distance field with respect to the centerline of the partial area of the blood vessel. According to the present exemplary embodiment, the distance transform may be presented as an image and may include information about the position of the centerline of the centerline of the partial area of the blood vessel for each pixel in the image. Accordingly, the medical imaging apparatus 100 or 200 may increase a speed of calculation of the distance between the centerline of each of the sub-blood vessel areas and the centerline of the partial area of the blood vessel, by using the distance transform with respect to the centerline of the partial area of the blood vessel, and the centerlines of each of the sub-blood vessel areas.

The medical imaging apparatus 100 or 200 according to the present exemplary embodiment may calculate the distance between the centerline of each of the sub-blood vessel areas and the centerline of the partial area of the blood vessel, and determine a sub-blood vessel area having the minimum distance from the partial area of the blood vessel, from among the sub-blood vessel areas. Accordingly, the medical imaging apparatus 100 or 200 may determine the sub-blood vessel area having the minimum distance from the partial area of the blood vessel, to be the blood vessel area in the 3D medical image having the highest similarity with the partial area of the blood vessel.

In S930, the medical imaging apparatus 100 or 200 matches the blood vessel area with the partial area of the blood vessel in the 2D medical image.

The medical imaging apparatus 100 or 200 according to the present exemplary embodiment may match the blood vessel area in the 3D medical image having the highest similarity with the partial area of the blood vessel in the 2D medical image with the 2D medical image. According to the present exemplary embodiment, the medical imaging apparatus 100 or 200 may determine transform information to match the blood vessel area in the 3D medical image with the partial area of the blood vessel in the 2D medical image. An example of the transform information may be a transformation matrix. According to the present exemplary embodiment, the medical imaging apparatus 100 or 200 may determine a transformation matrix to match the sub-blood vessel area in the 3D medical image with the partial area of the blood vessel, based on the information about the translational or rotational movement performed on the sub-blood vessel area having the minimum distance from the partial area of the blood vessel among the sub-blood vessel areas. In other words, the medical imaging apparatus 100 or 200 may determine may determine the transformation matrix to more precisely match the blood vessel area in the 3D medical image with the partial area of the blood vessel in the 2D medical image, by adding or subtracting a change amount within a preset range with respect to each figure of a matrix indicating the translational or rotational movement performed on the sub-blood vessel area. Accordingly, the medical imaging apparatus 100 or 200 may match the blood vessel area in the 3D medical image having the highest similarity with the partial area of the blood vessel with the 2D medical image, by using the determined transformation matrix. In addition, the medical imaging apparatus 100 or 200 may generate a match image in which the blood vessel area in the 3D medical image is matched with the 2D medical image.

Furthermore, according to the present exemplary embodiment, the medical imaging apparatus 100 or 200 may match a blood vessel area larger than the blood vessel area in the 3D medical image having the highest similarity with the partial area of the blood vessel with the 2D medical image, according to a user's selection.

Figure 10:
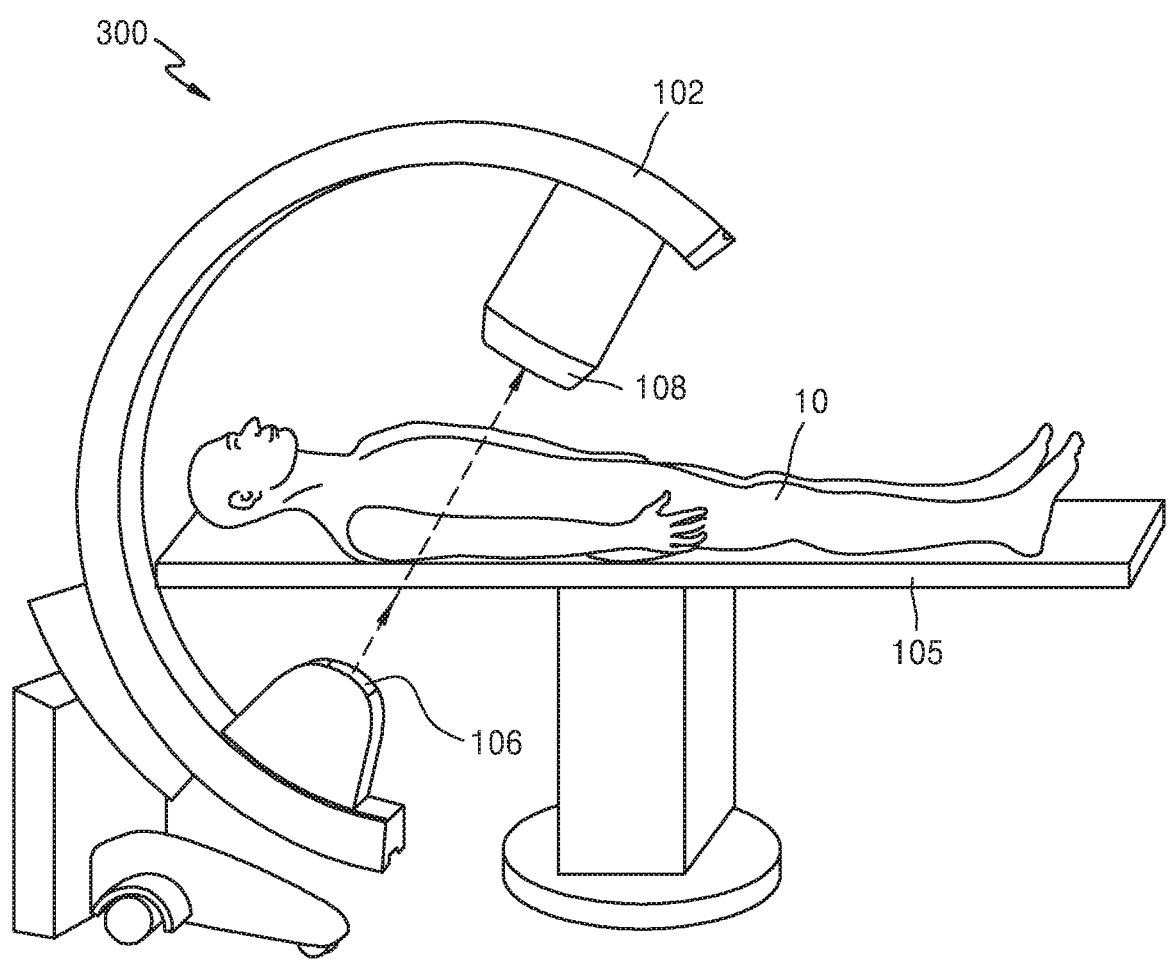
FIGS. 10 and 11 illustrate an X-ray apparatus according to an exemplary embodiment.
Figure 11:
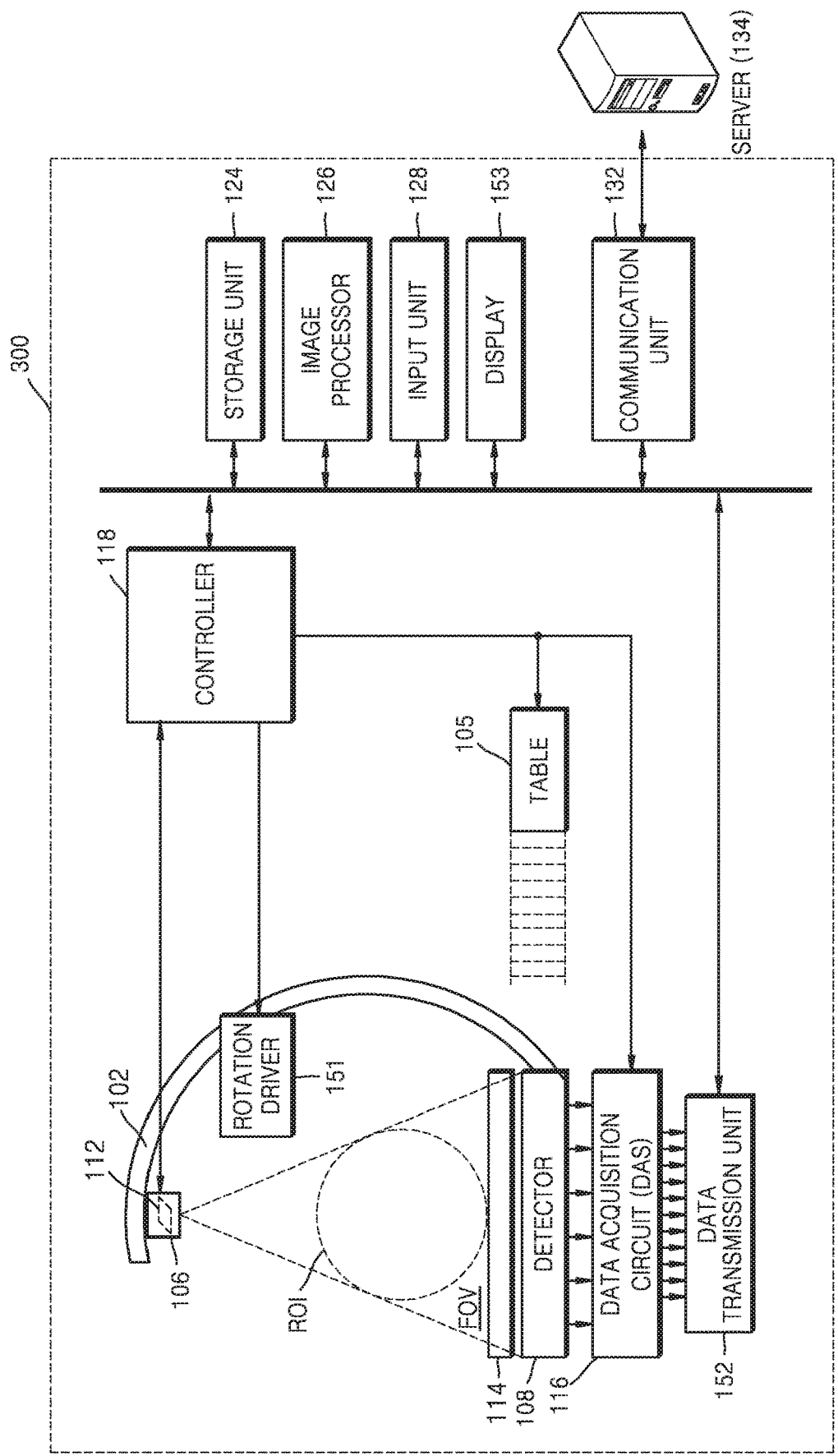

FIGS. 10 and 11 illustrate an X-ray apparatus 300 according to an exemplary embodiment.

The medical imaging apparatus 100 or 200 of FIGS. 1 and 2 may perform a part or all of functions of the X-ray apparatus 300 of FIGS. 10 and 11. The image acquirers 110 and 210 of FIGS. 1 and 2 may correspond to at least one of a detector 108, a data acquisition circuit 116, and a data transmission unit 152 of FIGS. 10 and 11. In addition, the matching units 120 and 220 of FIGS. 1 and 2 may correspond to the image processor 126 of FIG. 11. In addition, the display 230, the input unit 240, and the storage unit 250 of FIG. 2 may respectively correspond to a display 153, an input unit 128, and a storage unit 124 of FIG. 11.

Referring to FIG. 10, the X-ray apparatus 300 may include a C-arm 102 having a C shape and continuously performing X-ray imaging for a certain time period. An X-ray source 106 may be provided at one end of the C-arm 102 and a detector 108 may be provided at the other end of the C-arm 102. The C-arm 102 connects the X-ray source 106 and the detector 108 may adjust the positions of the X-ray source 106 and the detector 108. Although it is not illustrated in FIG. 10, the C-arm 102 may be coupled to a ceiling, a floor, or both of the ceiling and the floor. Also, the X-ray apparatus 300 may further include a table 105 where an object 10 may be located.

The X-ray source 106 is configured to generate and transmit an X-ray. The detector 108 is configured to detect the X-ray that is transmitted by the X-ray source 106 to transmit through the object 10. A medical image may be acquired based on the X-ray detected by the detector 108. While rotating, the X-ray source 106 may transmit an X-ray. The X-ray source 106 may be rotated as the C-arm 102 rotates. The detector 108 that rotates together with the X-ray source 106 may detect the X-ray that has transmitted through the object 10.

As the user adjust a position of at least one of the C-arm 102 and the table 105, the object 10 may be imaged at various positions or various angles. For example, while the user rotates or moves in four directions at least one of the C-arm 102 and the table 105, the object 10 is imaged thereby acquiring a medical image. Accordingly, the user may more efficiently image the object 10 using the X-ray apparatus 300 for a continuous time period, compared to a general fixed type X-ray apparatus.

The X-ray apparatus 300 may be useful when a plurality of X-ray images or an X-ray motion picture is to be acquired for a continuous time period. For example, the X-ray apparatus 300 may be useful in medical treatments such as an X-ray angiograpy or a surgical operation. When a medical doctor needs to carefully examine a patient with vascular disease to diagnose a disease, the medical doctor continuously performs X-ray imaging during an examination time. Then, a state of blood vessels of a patient is examined through a fluoroscopic image that is an X-ray motion picture acquired in real time. Accordingly, in a medical treatment such as angiography, an X-ray is continuously transmitted toward the object 10 during a treatment time to acquire a fluoroscopic image.

For example, for a case of angiography, X-ray imaging may be performed by installing a guide wire around an object. Alternatively, the X-ray imaging may be performed by injecting a drug using a thin needle or a catheter.

For another example, for a case of a surgical treatment, the treatment is performed by inserting a catheter, stent, or an injection needle into a human body. A user such as a medical doctor checks whether the catheter is accurately inserted in a target position of the object 10. Accordingly, the user may perform the treatment by acquiring a fluoroscopic image and checking the position of a target object such as a catheter through the acquired fluoroscopic image during the treatment.

The X-ray apparatus may an interventional X-ray apparatus, interventional angiography C-arm X-ray apparatus, or a surgical C-arm X-ray apparatus.

According to the present exemplary embodiment, the X-ray apparatus 300 may acquire a 3D medical image displaying a blood vessel in the object in 3D. In addition, the X-ray apparatus 300 may acquire a 2D medical image displaying a blood vessel in the object in 2D, by performing X-ray angiography on the blood vessel in the object. In other words, the user may inject a contrast agent into a blood vessel of an object and the X-ray apparatus 300 performs X-ray angiography, thereby acquiring a 2D medical image in which a portion of the blood vessel, into which the contrast agent is injected, is displayed. In addition, the X-ray apparatus 300 may determine a blood vessel area in the 3D medical image corresponding to the partial area of the blood vessel in the 2D medical image. Next, the X-ray apparatus 300 may match the blood vessel area in the 3D medical image with the partial area of the blood vessel in the 2D medical image.

Referring to FIG. 11, the X-ray apparatus 300 may include the X-ray source 106, the detector 108, and the C-arm 102 connecting the X-ray source 106 and the detector 108. Also, the X-ray apparatus 300 may further include a rotation driver 151, the data acquisition circuit 116, the data transmission unit 152, the table 105, a controller 118, the storage unit 124, the image processor 126, the input unit 128, the display 153, a communication unit 132.

The object 10 may be located on the table 105. The table 105 according to an exemplary embodiment may move in a certain direction, for example, at least one of up, down, left, and right directions, and the motion of the table 105 may be controlled by the controller 118.

The X-ray source 106 and the detector 108 connected to the C-arm 102 to face each other have a certain field of view (FOV). When the X-ray source 106 and the detector 108 are rotated by the C-arm 102, the FOV may be changed accordingly.

The X-ray apparatus 300 may further include an anti-scatter grid 114 located on the detector 108.

X-ray radiation arriving at the detector 108 may include not only attenuated primary radiation forming a useful image, but also scattered radiation degrading the quality of an image. The anti-scatter grid 114 may be located between a patient and a detector (or a photosensitive film) in order to transmit most of the primary radiation and attenuate the scattered radiation.

For example, the anti-scatter grid 114 may be configured in the form of alternately stacking strips of lead foil, a solid polymer material or solid polymer, and an interspace material such as a fiber composite material. However, the shape of the anti-scatter grid 114 is not necessarily limited thereto.

The C-arm 102 may receive a drive signal and power from the rotation driver 151, and rotate the X-ray source 106 and the detector 108 at a certain rotation speed.

The X-ray source 106 may generate and transmit an X-ray by receiving a voltage and current from a power distribution unit (PDU, not shown) through a high voltage generator (not shown). When the high voltage generator applies a certain voltage (hereinafter, referred to as the tube voltage) to the X-ray source 106, the X-ray source 106 may generate X-rays having a plurality of energy spectrums corresponding to the certain tube voltage.

An X-ray generated by the X-ray source 106 may be transmitted in a certain shape by a collimator 112.

The detector 108 may be located facing the X-ray source 106. The detector 108 may include a plurality of X-ray detection elements. A single X-ray detection element may form a single channel, but not limited thereto.

The detector 108 may detect the X-ray generated by the X-ray source 106 and transmitted through the object 10 and generate an electrical signal corresponding to the intensity of detected X-ray.

The detector 108 may include an indirect type detector that detect radiation by converting the radiation to light and a direct type detector that detect radiation by directly converting the radiation to electric charges. An indirect type detector may use a scintillator. Also, a direct type detector may use a photon counting detector. The data acquisition circuit 116 may be connected to the detector 108. The electrical signal generated by the detector 108 may be collected by the data acquisition circuit 116 in a wired or wireless manner. Also, the electrical signal generated by the detector 108 may be provided to an analog/digital converter (not shown) through an amplifier (not shown).

Only part of data collected by the detector 108 may be provided to the image processor 126 according to the thickness or number of slices, or the image processor 126 may select only part of data.

The digital signal may be provided to the image processor 126 through the data transmission unit 152 in a wired or wireless manner.

The controller 118 according to an exemplary embodiment may control an operation of each of modules included in the X-ray apparatus 300. For example, the controller 118 may control operations of the table 105, the rotation driver 151, the collimator 112, the data acquisition circuit 116, the storage unit 124, the image processor 126, the input unit 128, the display 153, and the communication unit 132.

The image processor 126 may receive the data acquired from the data acquisition circuit 116, for example, raw data before processing, through the data transmission unit 152, and perform a pre-processing process on the received data.

The pre-processing process may include, for example, a process of correcting irregular sensitivity between channels or a process of correcting signal loss due to radical decrease of signal intensity or an X-ray absorption member such as metal.

The pre-processed data by the image processor 126 may be referred to as raw data or projection data. The projection data may be stored in the storage unit 124 with imaging conditions for data acquisition, for example, the tube voltage or imaging angle.

The projection data may be a set of data values corresponding to the intensity of an X-ray transmitting through the object 10. For convenience of explanation, a set of the projection data simultaneously acquired at the same imaging angle with respect to all channels is referred to as a projection data set or measured data.

The storage unit 124 may include at least one type of storage unit media including flash memory type memory, hard disk type memory, multimedia card micro type memory, card type memory such as SD or XD memory, random access memory (RAM) static RAM (SRAM), read-only memory (ROM), electrically erasable programmable ROM (EEPROM), programmable ROM (PROM), magnetic memory, magnetic disc, and optical disc.

Also, the image processor 126 may acquire a reconstructed image of the object 10 based on the acquired measured data. The image processor 126 may acquire a reconstructed image that is acquired by imaging a ROI from the measured data. The ROI is an area that may be reconstructed by the X-ray apparatus 300 to an image. The reconstructed image may be 3D image. In other words, the image processor 126 may generate a 3D image of the object 10 based on the acquired measured data using a cone beam reconstruction method.

The input unit 128 may receive an external input such as X-ray tomography conditions, or image processing conditions. For example, the X-ray tomography conditions may include setting of a plurality of tube voltages and a plurality of energy values of X-rays, selecting an imaging protocol, selecting an image reconstruction method, setting an FOV area, setting an ROI area, setting the number of slices, slice thickness, and image post-processing parameters. Also the image processing conditions may include setting resolution of an image, setting an attenuation coefficient of an image, and setting a combination ratio of an image.

The input unit 128 may include a device to receive a certain input from the outside. For example, the input unit 128 may include a microphone, a keyboard, a mouse, a joystick, a touch pad, a touch pen, and a voice and gesture recognition device.

The display 153 may display an image reconstructed by the image processor 126.

The transmission and receiving of data or power between the above-described elements may be performed by using at least one of wired, wireless, and optical communication methods.

The communication unit 132 may perform communication with an external device or an external medical apparatus via a server 134. Alternatively, the X-ray apparatus 300 may be connected to a workstation (not shown) that is configured to control the X-ray apparatus 300, through the communication unit 132, which will be described later with reference to FIG. 12.

Figure 12:
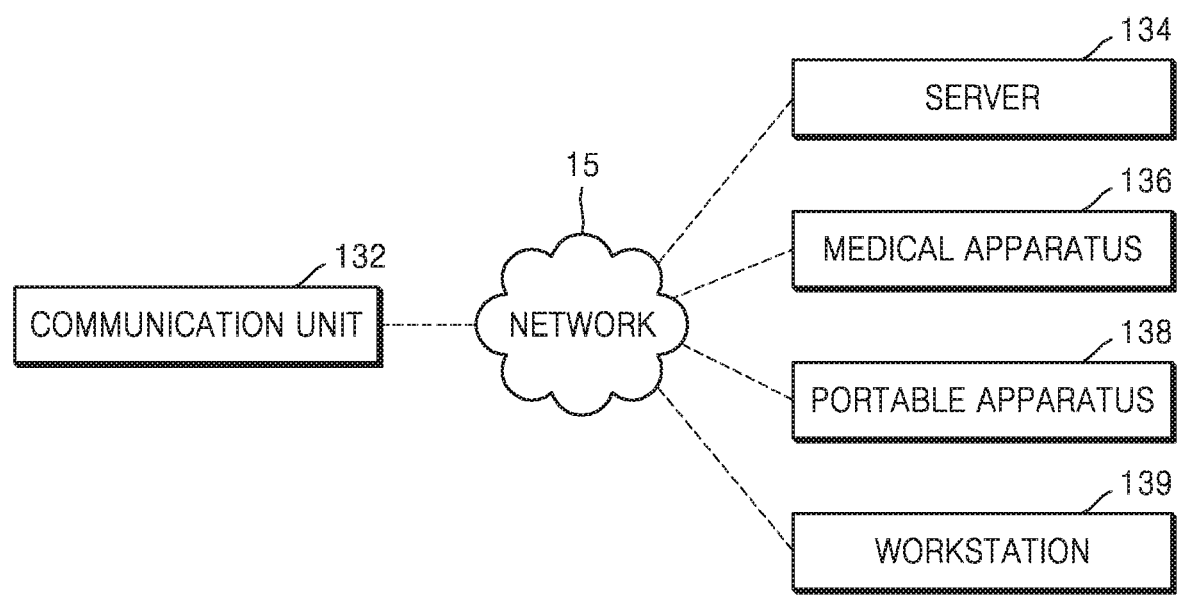
FIG. 12 illustrates a structure of a communication unit of FIG. 11.

FIG. 12 is a block diagram of a structure of the communication unit 132 of FIG. 11 according to an exemplary embodiment.

The communication unit 132 may be connected to a network 15 in a wired or wireless method and may perform communication with an external device such as the server 134, a medical apparatus 136, a portable apparatus 138, or a workstation 139. The communication unit 132 may exchange data with a hospital sever or other medical apparatuses in a hospital through a picture archiving and communication system (PACS) that is a medical image information system.

Also, the communication unit 132 may perform data communication with the portable apparatus 138 according to a digital imaging and communications in medicine (DICOM) that is a medical digital imaging and communication standard.

The communication unit 132 may transmit and receive data related to diagnose of the object 10 via the network 15. Also, the communication unit 132 may transmit or receive a medical image acquired by the medical apparatus 136, for example, an MRI apparatus or an X-ray apparatus.

Furthermore, the communication unit 132 may receive information about a diagnosis history or treatment schedule of a patient from the server 134 and use received information for clinical diagnosis of a patient. Also, the communication unit 132 may perform data communication not only with the server 134 or the medical apparatus 136 in a hospital, but also with the portable apparatus 138 of the user or a patient or the workstation 139.

Also, the communication unit 132 may transmit information about a status of equipment and a status of quality management to a system manager or a service manager via a network, and receive feedback thereon.

The workstation 139 may exist in a space physically separated from the X-ray apparatus 300. The X-ray apparatus 300 may exist in a shield room and the workstation 139 may exist in a console room. A shield room signifies a space where the X-ray apparatus 300 is located and the object 10 is imaged, and may be variously referred to as the "imaging room", the "examination laboratory", or the "examination room". Also, a console room is a space where the user is located to control the X-ray apparatus 300, which is separated from the shield room. The console room and the shield room may be separated from each other by a shielding wall to protect the user from a magnetic field, radiation, or a radio frequency (RF) signal transmitted from the shield room.

The device described herein may comprise a processor, a memory for storing program data and executing it, a permanent storage unit such as a disk drive, a communications port for handling communications with external devices, and user interface devices, including a touch panel, keys, buttons, etc. When software modules or algorithms are involved, these software modules may be stored as program instructions or computer-readable codes executable on a processor on a computer-readable recording medium. Examples of the computer-readable recording medium include magnetic storage media (e.g., ROM, RANI, floppy disks, hard disks, etc.), and optical recording media (e.g., CD-ROMs, digital versatile disks (DVDs), etc.). The computer-readable recording medium can also be distributed over network coupled computer systems so that the computer-readable code is stored and executed in a distributive manner. This media can be read by the computer, stored in the memory, and executed by the processor.

The present inventive concept may be described in terms of functional block components and various processing steps. Such functional blocks may be realized by any number of hardware and/or software components configured to perform the specified functions. For example, the present inventive concept may employ various integrated circuit (IC) components, e.g., memory elements, processing elements, logic elements, look-up tables, and the like, which may carry out a variety of functions under the control of one or more microprocessors or other control devices. Similarly, where the elements of the present inventive concept are implemented using software programming or software elements, the inventive concept may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the present inventive concept could employ any number of related techniques for electronics configuration, signal processing and/or control, data processing and the like. The words "mechanism," "element," "means," and "configuration" are used broadly and are not limited to mechanical or physical embodiments, but can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The present inventive concept is not limited to the described order of the steps. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to one of ordinary skill in the art without departing from the spirit and scope of the present inventive concept.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A method of processing a medical image, the method comprising:
    acquiring a three-dimensional (3D) medical image indicating a blood vessel and a two-dimensional (2D) medical image indicating the blood vessel;
    extracting a 3D blood vessel area from the 3D medical image;
    dividing the 3D blood vessel area into a plurality of sub-blood vessel areas;
    extracting a partial area of the blood vessel from the 2D medical image;
    selecting a target sub-blood vessel area having a highest similarity with the partial area in the 2D medical image from among the divided plurality of sub-blood vessel areas; and
    generating a match image by matching the selected target sub-blood vessel area in the 3D medical image with the partial area in the 2D medical image,
    wherein the match image comprises the selected target sub-blood vessel area excluding non-selected sub-blood vessel areas in the 3D medical image.

2. The method of claim 1, wherein the partial area is any one of an area, into which a contrast agent is injected, in a blood vessel of the 2D medical image, a region of interest (ROI) in a blood vessel of the 2D medical image, and an area where a target object is located in a blood vessel of the 2D medical image.

3. The method of claim 1, wherein the determining of the sub-blood vessel area further comprises:
    performing a translational or rotational movement on centerlines of each of the plurality of sub-blood vessel areas;
    calculating a distance between the translationally or rotationally moved centerlines of each of the plurality of sub-blood vessel areas and a centerline of the partial area; and
    determining the sub-blood vessel area having a distance of a minimum value from the partial area to be the blood vessel area.

4. The method of claim 1, wherein the selecting of the target sub-blood vessel area further comprises:
    projecting centerlines of each of the plurality of sub-blood vessel areas onto a 2D plane;
    calculating a distance between the projected centerline of each of the sub-blood vessel areas and a centerline of the partial area; and
    determining the target sub-blood vessel area having a distance of a minimum value from the partial area to be the blood vessel area.

5. The method of claim 4, wherein the calculating of the distance comprises:
    generating a distance transform with respect to the centerline of the partial area; and
    calculating a distance between the projected centerline of each of the sub-blood vessel areas and the centerline of the partial area, by using the distance transform.

6. The method of claim 1, wherein the matching of the sub-blood vessel area with the partial area in the 2D medical image comprises:
    determining 3D transform information to match the blood vessel area with the partial area; and
    matching the sub-blood vessel area with the partial area of the 2D medical image, based on the 3D transform information.

7. The method of claim 1, further comprising:
    storing the match image in which the sub-blood vessel area is matched with the partial area of the 2D medical image; and
    displaying the match image.

8. The method of claim 1, wherein the 3D medical image is an image acquired through computed tomography (CT) angiography before performing a certain operation on an object, and the 2D medical image is an image acquired through X-ray angiography during the operation performed on the object.

9. A computer readable recording medium having recorded thereon a program, which when executed by a computer, performs the method of claim 1.

10. The method of claim 1, wherein the selecting of the target sub-blood vessel area in the 3D medical image corresponding to the partial area of the blood vessel in the 2D medical image comprises:
    generating a graph corresponding to the 3D blood vessel area, based on a branch point of the blood vessel,
    dividing the graph corresponding to the 3D blood vessel area into a plurality of sub-blood vessel areas according to a certain condition, and
    determining the target sub-blood vessel area having a highest similarity with the partial area, from among the plurality of sub-blood vessel areas divided from the 3D blood vessel area.

11. A medical imaging apparatus comprising:
- an image acquirer configured to acquire a three-dimensional (3D) medical image indicating a blood vessel and a two-dimensional (2D) medical image indicating the blood vessel; and
- a matching unit configured to:
  - extract a 3D blood vessel area from the 3D medical image;
  - divide the 3D blood vessel area into a plurality of sub-blood vessel areas,
  - extract a partial area of the blood vessel from the 2D medical image,
  - select a target sub-blood vessel area having a highest similarity with the partial area in the 2D medical image from among the divided plurality of sub-blood vessel areas, and
  - generate a match image by matching the selected target sub-blood vessel area in the 3D medical image with the partial area of the 2D medical image,
  - wherein the match image comprises the selected target sub-blood vessel area excluding non-selected sub-blood vessel areas in the 3D medical image.

12. The medical imaging apparatus of claim 11, wherein the partial area is any one of an area, into which a contrast agent is injected, in a blood vessel of the 2D medical image, a region of interest (ROI) in a blood vessel of the 2D medical image, and an area where a target object is located in a blood vessel of the 2D medical image.

13. The medical imaging apparatus of claim 11, wherein the matching unit is further configured to:
- perform a translational or rotational movement on centerlines of each of the plurality of sub-blood vessel areas,
- calculate a distance between the translationally or rotationally moved centerlines of each of the plurality of sub-blood vessel areas and a centerline of the partial area, and
- determine the sub-blood vessel area having a distance of a minimum value from the partial area to be the blood vessel area.

14. The medical imaging apparatus of claim 11, wherein the matching unit is further configured to:
- project centerlines of each of the plurality of sub-blood vessel areas onto a 2D plane,
- calculate a distance between the projected centerline of each of the sub-blood vessel areas and a centerline of the partial area, and
- determine the target sub-blood vessel area having a distance of a minimum value from the partial area to be the blood vessel area.

* * * * *